United States Patent
Handie et al.

(10) Patent No.: US 9,993,246 B1
(45) Date of Patent: Jun. 12, 2018

(54) MEDICAL DEVICE BENDING DEVICES AND METHODS OF USE

(71) Applicants: Andronica Handie, Tulsa, OK (US); Daniel Lanois, Atlanta, GA (US)

(72) Inventors: Andronica Handie, Tulsa, OK (US); Daniel Lanois, Atlanta, GA (US)

(73) Assignee: ENDURE ENTERPRISES, PLLC, Tulsa, OK (US)

( * ) Notice: Subject to any disclaimer, the term of this patent is extended or adjusted under 35 U.S.C. 154(b) by 0 days. days.

(21) Appl. No.: 15/644,271

(22) Filed: Jul. 7, 2017

(51) Int. Cl.
*A61B 17/068* (2006.01)
*A61B 17/064* (2006.01)
*A61B 17/00* (2006.01)

(52) U.S. Cl.
CPC ........ *A61B 17/068* (2013.01); *A61B 17/0644* (2013.01); *A61B 2017/00477* (2013.01)

(58) Field of Classification Search
CPC .............. A61B 17/8863; A61B 17/068; A61B 17/0644
USPC ........................ 227/19, 82, 175.1, 176.1, 147
See application file for complete search history.

(56) References Cited

U.S. PATENT DOCUMENTS

| | | | |
|---|---|---|---|
| 2,544,492 A * | 3/1951 | Downing | A61B 17/10 227/181.1 |
| 4,438,769 A * | 3/1984 | Pratt | A61B 17/0642 227/147 |
| 7,635,367 B2 | 12/2009 | Groiso | |
| 8,137,351 B2 | 3/2012 | Prandi | |
| 8,211,109 B2 | 7/2012 | Groiso | |
| D669,984 S | 10/2012 | Cheney | |
| 9,017,331 B2 | 4/2015 | Fox | |
| 9,101,349 B2 * | 8/2015 | Knight | A61B 17/0642 |
| 2002/0173793 A1 | 11/2002 | Allen | |
| 2005/0273108 A1 | 8/2005 | Groiso | |
| 2010/0133316 A1 * | 6/2010 | Lizee | A61B 17/0642 227/175.1 |
| 2010/0237128 A1 | 9/2010 | Miller | |
| 2012/0228355 A1 | 9/2012 | Combrowski | |
| 2013/0206815 A1 | 8/2013 | Fox | |
| 2014/0034702 A1 | 4/2014 | Miller | |
| 2014/0097228 A1 * | 4/2014 | Taylor | A61B 17/0642 227/181.1 |
| 2014/0358187 A1 | 4/2014 | Taber | |
| 2014/0277516 A1 * | 9/2014 | Miller | A61B 17/0642 623/18.11 |
| 2015/0133940 A1 | 4/2015 | Palmer | |

(Continued)

FOREIGN PATENT DOCUMENTS

| WO | WO2008149308 | 12/2008 |
|---|---|---|
| WO | WO2010004602 | 1/2010 |

(Continued)

*Primary Examiner* — Nathaniel Chukwurah
(74) *Attorney, Agent, or Firm* — John M. Behles

(57) ABSTRACT

Medical device bending devices and methods of use are disclosed herein. An embodiment includes a body, a handle in rotatable relationship with the body, and a head that is coupled with the handle in such a way that when the handle is rotated the head is drawn at least partially into the body and towards the handle. A terminal end of the body that is opposite of the handle and the head cooperate as a vise that bends opposing arms of a surgical staple from an inwardly angled configuration to a parallel configuration (or at angles therebetween) when a crown of the surgical staple is clamped in the vise.

14 Claims, 5 Drawing Sheets

(56) References Cited

U.S. PATENT DOCUMENTS

| | | |
|---|---|---|
| 2015/0282819 A1 | 8/2015 | Austin |
| 2016/0199060 A1 | 7/2016 | Morgan |
| 2016/0235460 A1* | 8/2016 | Wahl .................. A61B 17/8863 |
| 2016/0338697 A1 | 11/2016 | Biedermann |

FOREIGN PATENT DOCUMENTS

| | | |
|---|---|---|
| WO | WO2015073642 | 5/2015 |
| WO | WO2016130842 | 8/2016 |

* cited by examiner

MEDICAL DEVICE BENDING DEVICES AND METHODS OF USE

FIELD OF THE PRESENT DISCLOSURE

Embodiments of the present disclosure are directed to surgical instruments, and more particularly, to but not by limitation, to medical device bending devices/apparatuses that are configured to bend, for example, surgical staples.

SUMMARY

According to some embodiments, the present disclosure is directed to a device, comprising: a body; a handle in rotatable relationship with the body; and a head that is coupled with the handle in such a way that when the handle is rotated, the head is drawn partially into the body and towards the handle, wherein a terminal end of the body that is opposite of the handle and the head cooperate as a vise, the vise clamping a crown of a surgical staple in such a way that ends of opposing arms of the surgical staple that extend from the crown move away from one another.

According to some embodiments, the present disclosure is directed to a method, comprising: inserting a surgical staple in a device, the device comprising: a body; a handle in rotatable relationship with the body; and a head that is coupled with the handle in such a way that when the handle is rotated, the head is drawn partially into the body and towards the handle, wherein a terminal end of the body that is opposite of the handle and the head cooperate as a vise that bends opposing arms of a surgical staple from the inwardly angled configuration to a parallel configuration when a crown of the surgical staple is clamped in the vise; and rotating the handle to transition the surgical staple from the inwardly angled configuration to a parallel configuration.

According to some embodiments, the present disclosure is directed to a kit, comprising: a surgical staple in an initial inwardly angled configuration (a shape memory material staple); and a device comprising: a body; a handle in rotatable relationship with the body; and a head that is coupled with the handle in such a way that when the handle is rotated, the head is drawn partially into the body and towards the handle, wherein a terminal end of the body that is opposite of the handle and the head cooperate as a vise that bends opposing arms of a surgical staple from the inwardly angled configuration to a parallel configuration when a crown of the surgical staple is clamped in the vise.

The kit can also include a pilot hole jig and pilot hole drill for creating pilot holes in a patient. The pilot hole jig has jig cylinders spaced apart from one another so as to create spacing between the pilot holes that correspond to a spacing of ends of the surgical staple when in the parallel configuration.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DESCRIPTION OF EXEMPLARY EMBODIMENTS

The present disclosure is directed, in some embodiments, to surgical apparatuses, devices, kits, and methods of use that allow a user to bend surgical staples from a first configuration to a second configuration. When in the second configuration, the surgical staple can be inserted into a patient to secure structures together. Example structures include bone, skin, cartilage, and other similar structures that would be known to one of ordinary skill in the art with the present disclosure before them.

In some embodiments, an example surgical device comprises a body that is configured to be gripped by a user. The surgical device also comprises a handle in rotatable relationship with the body. In various embodiments, the surgical device comprises a head that is coupled with the handle in such a way that when the handle is rotated, the head is drawn partially into the body and towards the handle.

In one or more embodiments, the handle is rotatably coupled with the head such that turning of the handle results in upward (e.g., towards the handle) movement of the head.

With respect to the bending of a surgical staple, the body and head of the surgical device form a vise that bends a crown of the surgical staple causing arms of the surgical staple to transition from an inwardly angled configuration to a parallel configuration. That is, the surgical staple is transitioned when the handle is turned, which results in the head being drawn towards a terminal end of the body, thereby pinching or compressing the crown of the staple.

Stated otherwise, the vise clamps a crown of a surgical staple in such a way that ends of opposing arms of the surgical staple that extend from the crown move away from one another.

The devices of the present disclosure are adapted to bending medical devices, such as surgical staples that are manufactured from shape memory alloy material. When the staple is removed from an example device after insertion of the surgical staple into the patient, the surgical staple returns to its initial configuration due to its shape memory material properties.

These and other advantages of the present disclosure are described in greater detail infra with respect to the collective drawings FIGS. 1-5.

Figure 1:
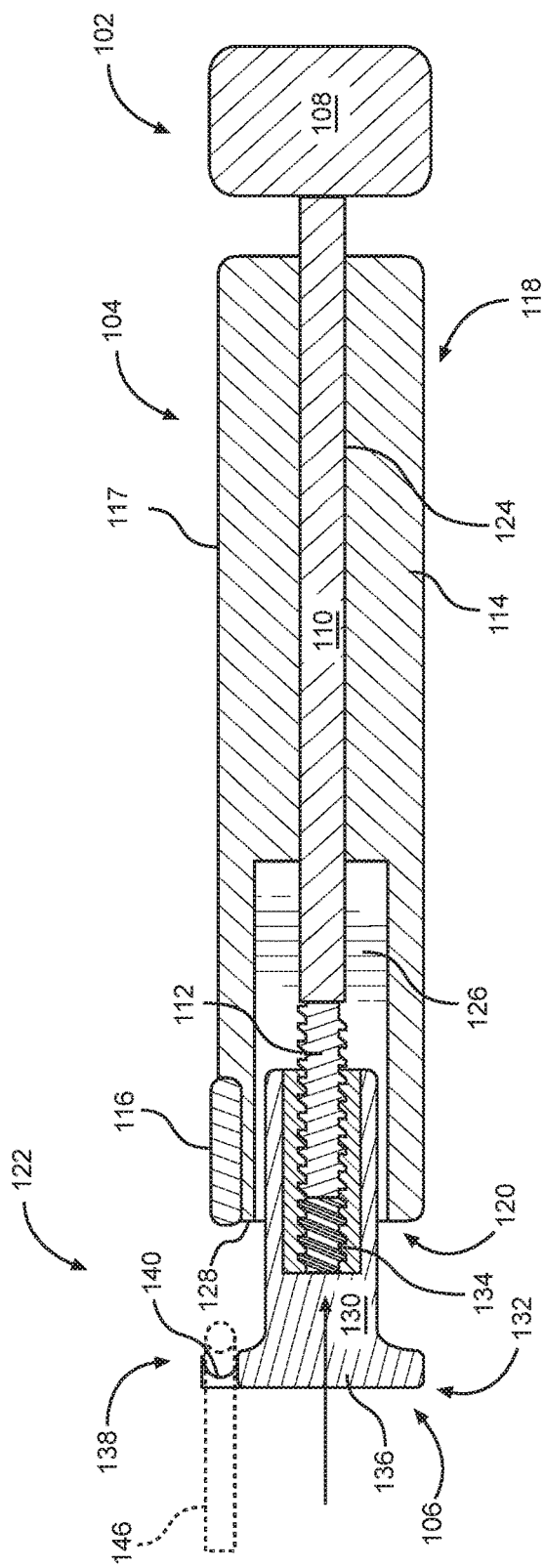
FIG. 1 is a cross-sectional view of an example device constructed in accordance with the present disclosure.

FIG. 1 is a cross sectional view of an example device 100, such as a surgical staple bending apparatus. The device 100 generally comprises a handle assembly 102, a body assembly 104, and a head assembly 106. In some embodiments, the handle assembly 102 comprises a handle 108 and a shaft 110. In various embodiments, the shaft 110 has a threaded end 112 that is configured for threaded engagement of the head assembly 106, as will be discussed in greater detail infra.

According to some embodiments, the shaft 110 is inserted through the body assembly 104 allowing the handle 108 to rotate about a first end or handle end of the body assembly 104.

Turning to the body assembly 104; it comprises a body 114 and protrusion 116 that forms a first portion of a vise 122. In some embodiments, the body 114 comprises a handle end 118 and a terminal end 120 that is opposite to the handle end 118. In some embodiments, the body 114 has curved surfaces that allow a user to easily grip and/or manipulate the body 114 (and by extension the device 100).

In accordance with the present disclosure, the body 114 comprises a linear passage 124 that provides a pathway from the handle end 118 to the terminal end 120. The linear passage 124 can comprise a cylindrical aperture that is sized to receive the shaft 110 of the handle assembly 102. The shaft 110 can freely rotate within the linear passage 124 based on rotation of the handle 108.

Also, the body 114 comprises a recess 126 that receives a portion of the head assembly 106.

Figure 4:
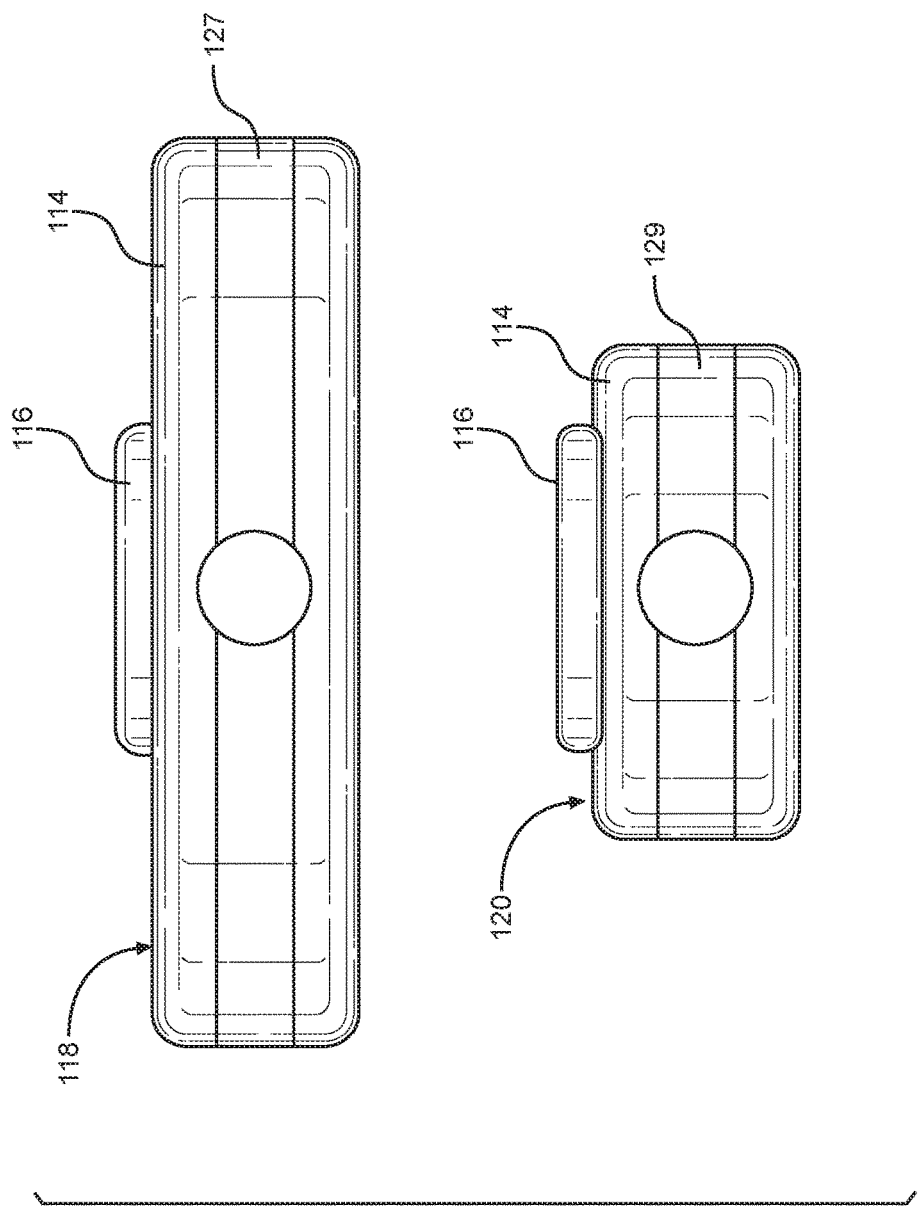
FIG. 4 illustrates plan views of the body of the example device of FIG. 1.

Referring briefly to FIG. 4, the body 114 comprises a channel 127 on the handle end 118, as well as a channel 129 on the terminal end 120. The device 100 can comprise either or both channels 127 and 129. Functionally, the channels provide mating interfaces that receive a portion of a surgical staple and allow the device 100 to be used as a tool for imparting percussive force to the surgical staple. These features are described in greater detail herein.

In one or more embodiments, the protrusion 116 comprises a hemispherical protrusion that at least partially overhangs a terminal end edge 128. The protrusion 116 also extends above an upper surface 117 of the body 114.

The head assembly 106, in some embodiments, comprises a dowel 130 and a block 132. The dowel 130 is configured for sliding insertion into the recess of the body 114. The dowel 130 comprises, in various embodiments, a threaded receiver 134. The threaded end 112 of the shaft 110 engages with the threaded receiver 134.

Rotation of the handle 108 in a first direction causes the threaded end 112 to drive into the threaded receiver 134, causing the dowel 130 to be drawn inwardly into the recess 126 (towards the handle 108) and the block 132 towards the terminal end 120 of the body 114. Rotation of the handle 108 in a second direction that is opposite of the first direction causes the threaded end 112 to be extracted from the threaded receiver 134, allowing the dowel 130 and block 132 to translate away from the handle 108.

Figure 3:
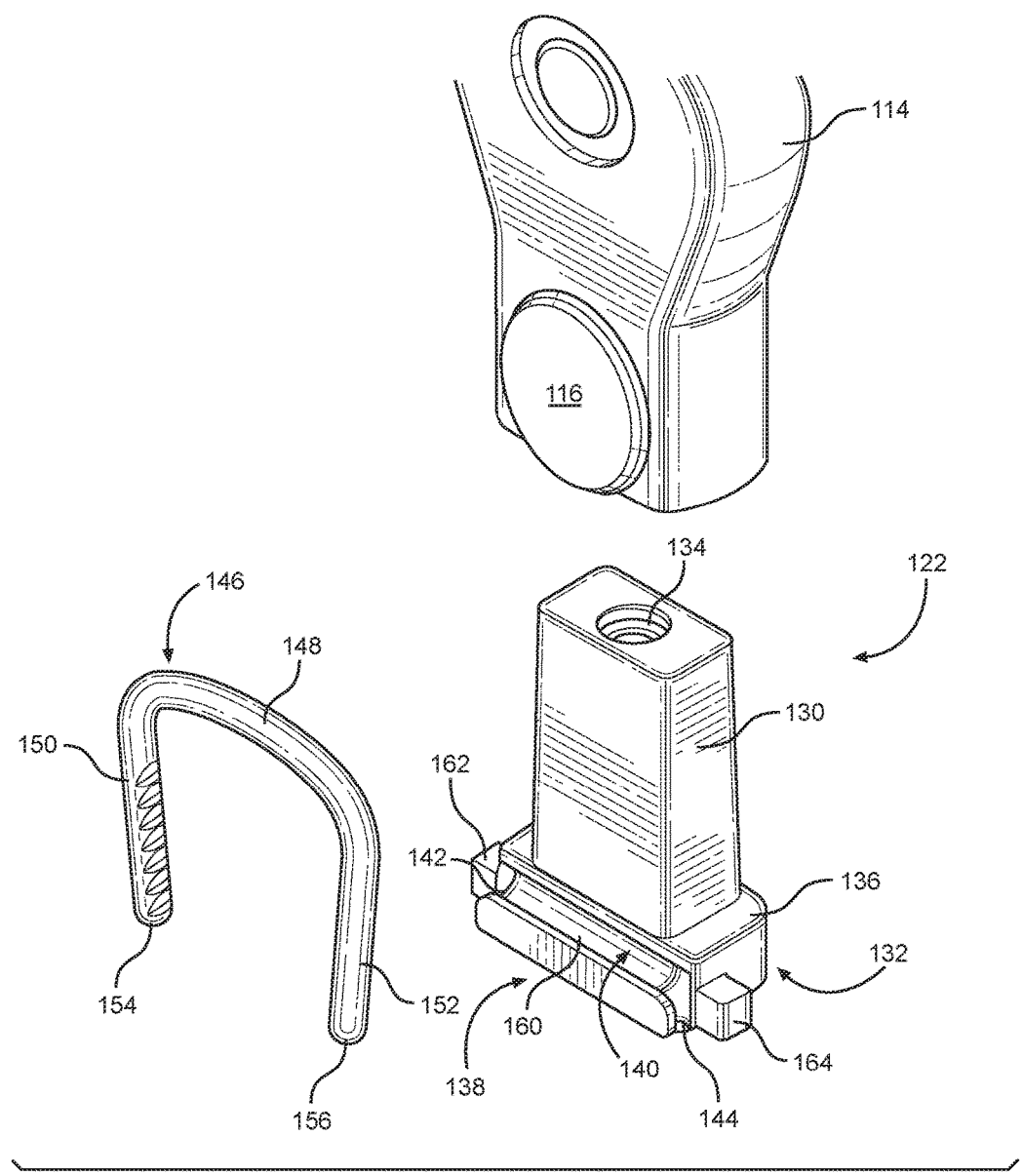
FIG. 3 is a perspective view of a head assembly of the device of FIG. 1.

Referring briefly to FIG. 3, according to some embodiments the block 132 functions as a second portion of the vise 122. In some embodiments, the block 132 comprises a flange 136 that extends from the dowel 130. Disposed on the flange 136 is a staple interface 138. The staple interface 138 comprises a groove 140 that is formed into a portion of the staple interface 138 at a terminal end of the flange 136.

In some embodiments, the groove 140 comprises rounded or arcuate ends 142 and 144.

Figure 2:
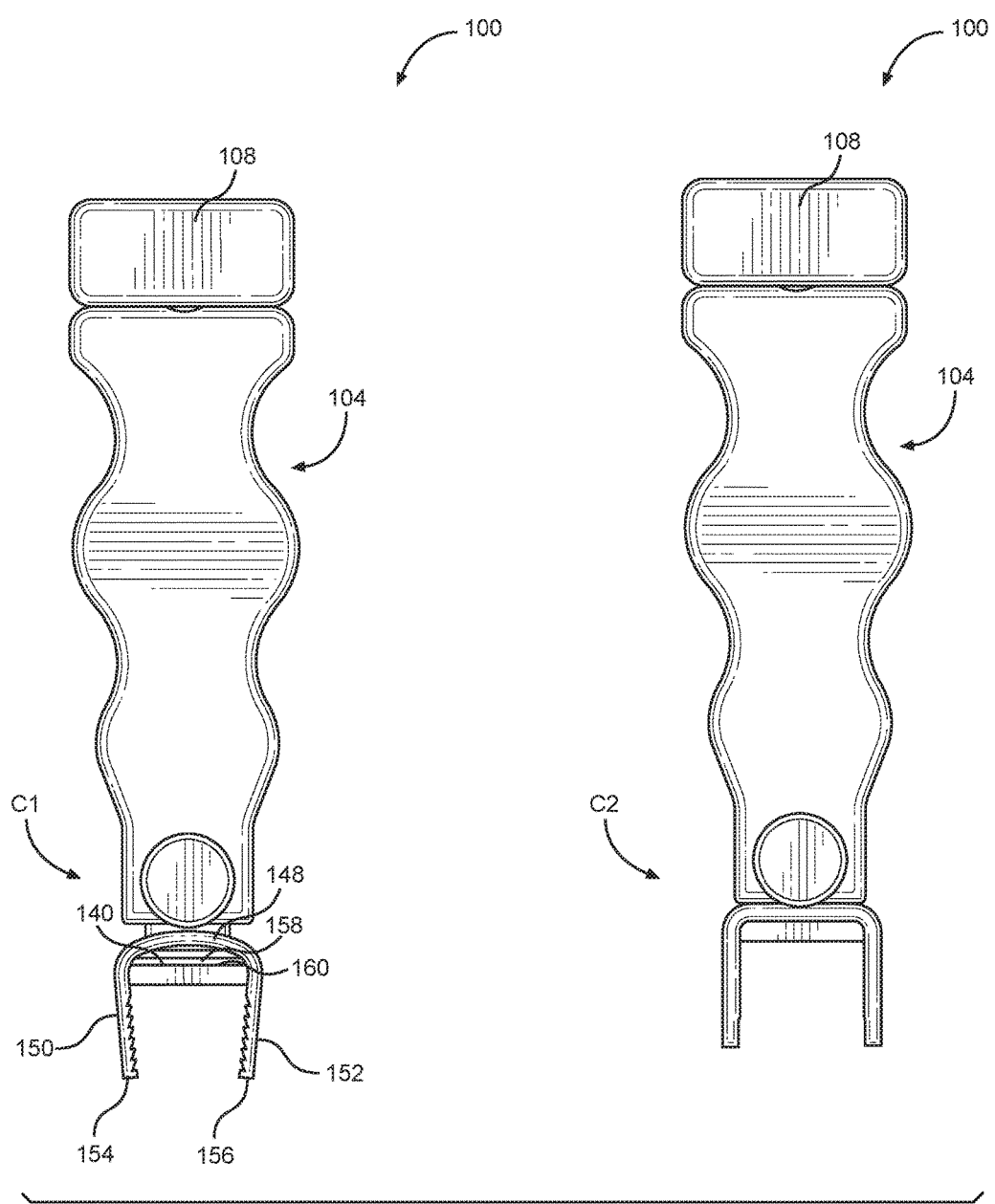
FIG. 2 includes plan views of the example device of FIG. 1 in combination with a surgical staple, where the surgical staple is in an initial, inwardly bent configuration and a parallel configuration.

Referring to FIGS. 1-3 collectively, the protrusion 116 of the body 114 and the groove 140 are coplanar with one another (as best illustrated in FIG. 1).

A surgical staple 146 can be cradled and held in place within the groove 140, as illustrated in FIG. 1, where the surgical staple is illustrated in phantom dotted line so that the groove 140 is viewable. More specifically, and turning to FIG. 3, the surgical staple 146 comprises a crown 148 and two arms 150 and 152. Each of the arms 150 and 152 has an end. For example, arm 150 has an end 154 and the arm 152 has an end 156.

Turning now to FIG. 2, the surgical staple 146 is initially in an inwardly angled configuration C1 where the crown 148 is arcuate and the ends 154 and 156 bend inwardly towards one another.

When surgical staple 146 is placed into the groove 140 in its inwardly angled configuration C1, the arcuate shape of the crown 148 allows for a space or gap 158 to exist between the crown 148 and a substantially linear portion 160 of the groove 140. This space 158 allows the crown 148 to deflect towards the substantially linear portion 160 of the groove 140 when the surgical staple 146 is clamped in the vise 122. Moreover, when the crown 148 is clamped in the vise 122, the crown 148 will begin to straighten into a linear configuration from its original arcuate configuration. Clamping of the crown 148 of the surgical staple 146 will cause the ends 154 and 156 to splay and/or move away from one another. This can result in the arms 150 and 152 transitioning to a substantially parallel configuration C2 (see FIG. 2). To be sure, not all embodiments and use cases require the surgical staple 146 to be in the substantially parallel configuration C2. Therefore, transitioning the surgical staple from the inwardly angled configuration C1 to an intermediate configuration that is less than the substantially parallel configuration C2 is also contemplated.

According to some embodiments, and turning to FIG. 3, the block 132 comprises a pair of protrusions 162 and 164 that extend laterally from the block 132. These protrusions are disposed behind the groove 140. When the surgical staple 146 is coupled with the groove 140, a portion of the surgical staple 146 abuts or contacts the protrusions 162 and 164. These protrusions 162 and 164 are optional in some embodiments. The protrusions can be used to support or stabilize the surgical staple 146 during bending and/or insertion.

The device 100 can be comprised of any suitable material that is capable of being used in a surgical operation. Some embodiments can be manufactured from materials that are amenable to sterilization and other embodiments may be manufactured from materials that allow for sterilization and reuse.

In operation, a user can utilize the device 100 to bend the surgical staple 146. The user can ensure that a space is created between the terminal end 120 of the body 114 and the groove 140 of the block 132 of the head assembly 106 so that the surgical staple 146 can be inserted into the groove 140 of the block 132. Once in position, the user can begin to turn the handle 108 which rotates the shaft 110 causing the threaded end 112 to drive into the threaded receiver 134 of the dowel 130. This in turn, causes the dowel 130 to translate upwardly into the recess 126 of the body 114 towards the handle 108. Upward movement of the dowel 130 causes the block 132 to be drawn into proximity of the protrusion 116 on the body 114. The surgical staple 146 begins to bend when the crown 148 is clamped between the protrusion 116 of the body 114 and the groove 140 of the block 132. In more detail, as the block 132 brings the crown 148 into contact with the protrusion 116, the gap 158 between the crown 148 and the groove 140 begins to reduce in size. As the crown 148 is compressed between the block 132 and the protrusion 116, the ends 154 and 156 begin to move away from one another.

When the handle 108 has been turned enough so that it contacts the handle end 118 of the body 114, the crown 148 is approximately compressed flatly (or is in mating contact in some embodiments) against the substantially linear portion 160 of the groove 140. In this position, the arms 150 and 152 of the surgical staple 146 are approximately parallel (or completely parallel) with one another. Stated otherwise, the compression of the crown 148 of the surgical staple 146 between the protrusion 116 and block 132 causes the arms 150 and 152 to splay outwardly from the inwardly angled configuration C1 to the parallel configuration C2.

In some embodiments, the shaft 110 is sized in length such that when the handle 108 contacts the handle end 118 of the body 114, the crown 148 of the surgical staple 146 is compressed between the block 132 and the protrusion 116 to place the arms 150 and 152 in parallel relationship to one another. Contact between the handle 108 and the handle end 118 of the body 114 then prevents further rotation of the handle 108, which could lead to over compression of the crown 148 of the surgical staple 146 (e.g., over-bending of the surgical staple 146). Thus, the length of the shaft 110 can vary such that the surgical staple 146 cannot be bent further than required. This could be based on spacing between pilot holes that receive the arms 150 and 152 of the surgical staple 146. The details of creating the pilot holes are described in greater detail infra.

When inserted into the patient, the device 100 can be decoupled from the surgical staple 146 by rotating the handle 108 in an opposing direction from the direction used to bend the surgical staple 146. When the handle 108 is rotated in the reverse direction, the shaft 110 rotates so as to begin to back out of the threaded receiver 134 of the dowel 130. This causes the dowel 130 to move away from the handle 108, which in turn causes the block 132 and the protrusion 116 to separate. When the block 132 and the protrusion 116 are sufficiently separated, the surgical staple 146 is removed from the block 132. In accordance with the present disclosure, the surgical staple 146 can be driven further into the patient using the body 114 of the device 100.

For example, the handle 108 and head assembly 106 can be removed from the body 114. Either of the channels 127 or 129 can be mated with the crown 148 of the surgical staple 146. That is, the crown 148 fits into whichever channel is selected. The user then applies a percussive force to an opposing end of the body 114 that is not engaged with the crown 148 driving the surgical staple 146 further into the patient, such as into a bone of the patient.

Figure 5:
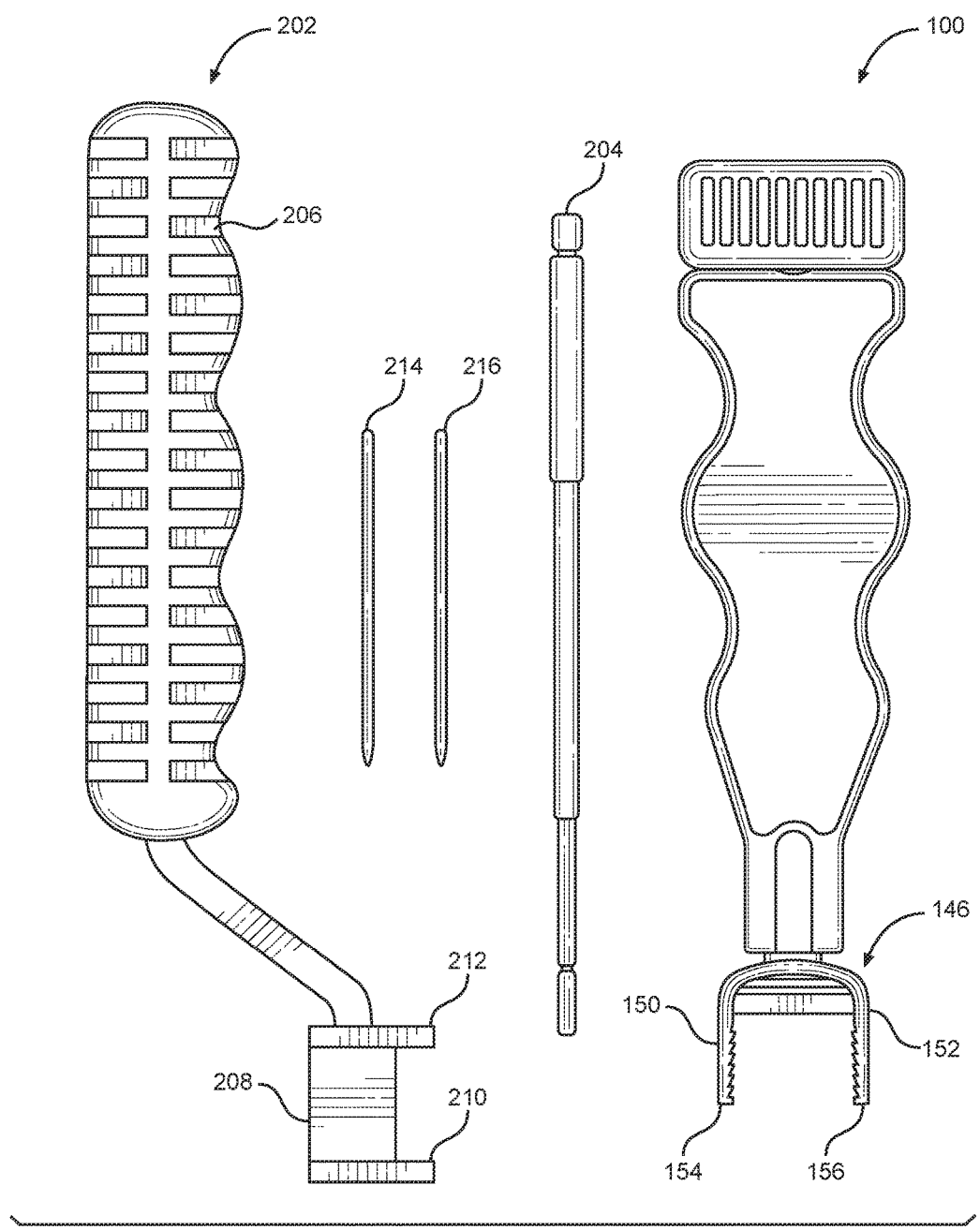
FIG. 5 is a perspective view of a kit comprising the device of FIG. 1 in combination with a pilot hole jig tool and a pilot hole drill bit.

FIG. 5 illustrates an example kit that comprises a device 100 of the present disclosure in combination with a pilot hole device 202 and pilot drill bit 204. In some embodiments, the pilot hole device 202 comprises a handle 206 and pilot hole jig 208. The pilot hole jig 208 comprises jig cylinders 210 and 212 that are spaced apart from one another. The pilot drill bit 204 is used to create pilot holes in a patient structure, such as a bone. That is, when the pilot hole jig 208 is positioned on the patient structure, the pilot drill bit 204 is inserted into each of the jig cylinders 210 and 212 respectively. The pilot drill bit 204 is used to ream out pilot holes in the patient structure.

As mentioned above, spacing between the jig cylinders 210 and 212 is set so as to correspond to spacing between arms 150 and 152 (or ends 154 and 156) of the surgical staple 146.

After creation of the pilot holes, the surgical staple 146 is bent in the device 100 according to the method described supra. The arms 150 and 152 of the surgical staple 146 are then inserted into the pilot holes.

In some embodiments, the kit further comprises one or more spikes 214 and 216 that are used to fill pilot holes after creation with the pilot hole jig 208 and the pilot drill bit 204.

Example uses for the devices of the present disclosure include, but are not limited to orthopedic procedures. For example, the devices of the present disclosure can be used to fuse or secure together separated segments of a bone, such as two sections of a broken metatarsal bone. The user can place the pilot hole jig 208 onto mating ends of the broken metatarsal bone and pilot holes are drilled. A surgical staple is then inserted into the pilot holes. It will be understood that the surgical staple is bent prior to insertion into the pilot holes. In some embodiments, the surgical staple is manufactured from a resiliently biased or shape memory material such as Nitinol™ The material properties of the surgical staple cause the surgical staple to return to its initial configuration (e.g., inwardly bent configuration C1, see FIG. 2), which draws the mating ends of the broken metatarsal bone toward one another and holds the mating ends together to promote fusion.

While this technology is susceptible of embodiment in many different forms, there is shown in the drawings and has been described in detail several specific embodiments with the understanding that the present disclosure is to be considered as an exemplification of the principles of the technology and is not intended to limit the technology to the embodiments illustrated.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A device, comprising:
   a body comprising a hemispherical protrusion that comprises a first portion of a vise;
   a handle in rotatable relationship with the body; and
   a head comprising a dowel and a block, the block comprising a second portion of the vise, wherein the head is coupled with the handle in such a way that when the handle is rotated the head is drawn at least partially into the body and towards the handle, wherein a terminal end of the body that is opposite of the handle and the head cooperate as a vise that bends opposing arms of a surgical staple from an inwardly angled configuration to a parallel configuration when a crown of the surgical staple is clamped in the vise.

2. The device according to claim 1, further comprising a threaded shaft that couples the handle and the head.

3. The device according to claim 2, wherein the body comprises a linear passage that receives the threaded shaft.

4. The device according to claim 3, wherein an end of the threaded shaft is threaded onto the head.

5. The device according to claim 1, wherein the body comprises a recess that receives a dowel of the head.

6. The device according to claim 1, wherein the hemispherical protrusion overhangs a terminal end edge.

7. The device according to claim 1, wherein the head comprises lateral protrusions that stabilize the surgical staple.

8. The device according to claim 7, wherein a threaded shaft comprises a length such that when the handle is rotated to draw the head upwardly towards the handle, the handle contacts the body to prevent over bending of the surgical staple beyond the parallel configuration.

9. The device according to claim 1, further comprising a first channel extending along a handle end of the body.

10. The device according to claim 9, further comprising a second channel extending along the terminal end of the body.

11. A kit, comprising:
    a surgical staple in an initial inwardly angled configuration;
    and a device comprising:
      a body comprising a hemispherical protrusion that comprises a first portion of a vise;
      a handle in rotatable relationship with the body; and
      a head comprising a dowel and a block, the block comprising a second portion of the vise, the head being coupled with the handle in such a way that when the handle is rotated the head is drawn partially into the body and towards the handle, wherein a terminal end of the body that is opposite of the handle and the head cooperate as a vise that bends opposing arms of a surgical staple from the inwardly angled configuration to a parallel configuration when a crown of the surgical staple is clamped in the vise.

12. The kit according to claim 11, further comprising a pilot hole jig and pilot hole drill for creating pilot holes in a patient, the pilot hole jig having jig cylinders spaced apart from one another so as to create spacing between the pilot holes that correspond to a spacing of ends of the surgical staple when in the parallel configuration.

13. The kit according to claim 12, further comprising one or more spikes that fill one or more of the pilot holes prior to insertion of the surgical staple in the pilot holes.

14. A device, comprising:
   a body;
   a handle in rotatable relationship with the body; and
   a head that is coupled with the handle in such a way that when the handle is rotated the head is drawn at least partially into the body and towards the handle, wherein a terminal end of the body that is opposite of the handle and the head cooperate as a vise that bends opposing arms of a surgical staple from an inwardly angled configuration to a parallel configuration when a crown of the surgical staple is clamped in the vise, wherein a block of the head comprises a groove having arcuate ends, the groove receiving a portion of the surgical staple.

* * * * *